United States Patent [19]
Greenberg

[11] Patent Number: 5,976,072
[45] Date of Patent: Nov. 2, 1999

[54] COPA METHOD FOR FIBEROPTIC ENDOTRACHEAL INTUBATION

[75] Inventor: Robert S. Greenberg, Glenelg, Md.

[73] Assignee: Johns Hopkins University, Baltimore, Md.

[21] Appl. No.: 09/015,219

[22] Filed: Jan. 29, 1998

[51] Int. Cl.$^6$ ..................................................... A61B 1/04
[52] U.S. Cl. .................................... 600/120; 128/207.14
[58] Field of Search ..................................... 600/120, 114, 600/115, 116, 117; 128/207.14, 898

[56] References Cited

U.S. PATENT DOCUMENTS

| | | | |
|---|---|---|---|
| 3,776,222 | 12/1973 | Smiddy | 600/120 X |
| 4,846,153 | 7/1989 | Berci | 600/120 X |
| 5,443,063 | 8/1995 | Greenberg . | |
| 5,653,229 | 8/1997 | Greenberg . | |
| 5,665,052 | 9/1997 | Bullard | 600/120 X |

OTHER PUBLICATIONS

Ovassapian, Andranik; *Fiberoptic Tracheal Intubation in Adults; Fiberoptic Endoscopy and the Difficult Airway*; Chapter 6, pp. 71–103.
Ovassapian, Andranik; *Pediatric Fiberoptic Intubation; Fiberoptic Endoscopy and the Difficult Airway*; Chapter 7, pp. 105–115.
Ovassapian, et al; *Fiberoptic Tracheal Intubation with Combitube in Place*; Anesth Analg 1993;76;S1–S476.
Ozaki, et al.; *Direction Dependence of Thermoregulatory Vasoconstriction During Isoflurane–Epidural Anesthesia*; Anesth Analg 1993;76;S1–S476.
Benumof Jonathan L.; *Fiberoptic Tracheal Intubation With The Combitube in Place*; Airway Management; pp. 252–253.
Ovassapian, Andranik and Wheeler, Melissa; *Fiberoptic Endoscopy–Aided Techniques*; Chapter 16, p. 319.

*Primary Examiner*—Beverly M. Flanagan
*Attorney, Agent, or Firm*—Pillsbury Madison & Sutro LLP

[57] ABSTRACT

For fiberoptic endotracheal intubation, a method is disclosed that uses a device having a cannula with a first, distal end for placement within the pharynx of a patient, a second, proximal end for being disposed outside of the patient's oral cavity, and a flow passage between the first and second ends. The cannula has a length such that, when the distal end is placed within the pharynx, it terminates distally at a point near the patient's epiglottis. The device includes an inflatable cuff structure for forming a seal between a wall of the cannula and the patient's pharynx. The cuff is positioned adjacent to the distal end of the device and defines, on inflation, a ventral/anterior portion and a posterior portion. The method involves a step of inserting the device, with cuff deflated, into a patient's mouth so that the distal end of the device is disposed at a point near the patient's epiglottis to establish an airway column down the core of the device. Once the cuff structure is inflated, the patient's airway is supported to provide spontaneous breathing and controlled ventilation through the flow passage of the device. Then, a fiberoptic scope, on which an endotracheal tube has been preloaded so that the distal tip of the scope projects beyond the endotracheal tube, is inserted into the patient through the patient's oral cavity so that the lip is in the throat past the uvula, whereby after insertion of the device and insertion of the fiberoptic scope, the scope is disposed exteriorly of the device. Then, the tip of the fiberoptic scope is advanced so that it enters the trachea. The endotracheal tube is then advanced through the oral cavity and into the trachea using the fiberoptic scope as a guide. Finally, the fiberoptic scope is removed from the trachea.

20 Claims, 2 Drawing Sheets

COPA METHOD FOR FIBEROPTIC ENDOTRACHEAL INTUBATION

BACKGROUND OF THE INVENTION

1. Field of the Invention

The present invention relates to fiberoptic endotracheal intubation and, more particularly, to a method for fiberoptic endotracheal intubation using a cuffed oro-pharyngeal airway (COPA).

2. Description of the Related Art

Fiberoptic endotracheal intubation has been used for several years and may be performed orally or nasally. Conventional methods of fiberoptic endotracheal intubation use the internal passage of a device, such as a laryngeal masked airway, Combitube®, Ovassapian Airway, or the like. The main disadvantage of passing the fiberoptic scope through an airway device is the increased airway resistance encountered, since the fiberscope occupies a significant portion of the lumen of the device. Moreover, it is impossible with such techniques to provide continuous airway support, either controlled inspired gas concentration or assisted/controlled positive pressure manual ventilation.

Fiberoptic intubation with the patient under general anesthesia presents special problems. The main disadvantage of intubation under general anesthesia is that the tongue and pharyngeal tissues lose their tonicity and close down the pharyngeal space, blocking visualization of the larynx. Thus, in such circumstances, to minimize apnea time, and to facilitate laryngeal exposure, an assistant is required.

SUMMARY OF THE INVENTION

The disclosed method uses the exterior of a cuffed oro-pharyngeal airway (COPA), preferably of the type described in U.S. Pat. Nos. 5,653,229 and 5,443,063, the disclosures of which are incorporated herein by this reference, between the cuff and the pharyngeal wall to stabilize the fiberoptic scope. Using the COPA as an adjunct for fiberoptic endotracheal intubation allows control and support of the airway during the procedure, using various anesthetic techniques, in an acceptable amount of time, which would be expected to decrease with experience. The ability to perform fiberoptic endotracheal intubation while effectively supporting the airway using the COPA may be advantageous in managing the difficult airway and in teaching the technique of fiberoptic endotracheal intubation.

The disclosed techniques take advantage of the upper airway distending effects of the COPA cuff and ability for continuous ventilation. In fact, using the COPA cuff appropriately with the fiberoptic scope outside it, it is possible to have the cuff augment the size of the hypopharynx, lift the epiglottis, and facilitate fiberoptic intubation.

The COPA may be used both for oral endotracheal intubation and for nasal endotracheal intubation. Indeed, using the cuffed oro-pharyngeal airway during intubation with a fiberoptic scope allows airway support and assists in spontaneous breathing or controlled ventilation while positioning the fiberoptic scope from either the oral or nasal approach.

Conformability of the surrounding tissues and the cuff relative to the fiberoptic scope enables passage of the scope behind or on the outside of the COPA cuff without significant interference with its seal. Thus, positive pressure ventilation and special assistance in spontaneous ventilation can still be managed during fiberoptic laryngoscopy and endotracheal intubation.

As noted above, performance of the fiberoptic technique using the COPA allows the administration of oxygen or other gases or vapors, and does not require that the patient be apenic for each fiberoptic attempt. This is one of the major advantages of the method.

Other objects, features and characteristics of the present invention, will become more apparent upon consideration of the following detailed description and the appended claims with reference to the accompanying illustrations, all of which form a part of this specification.

DETAILED DESCRIPTION OF THE PRESENTLY PREFERRED EXEMPLARY EMBODIMENTS

Figure 1:
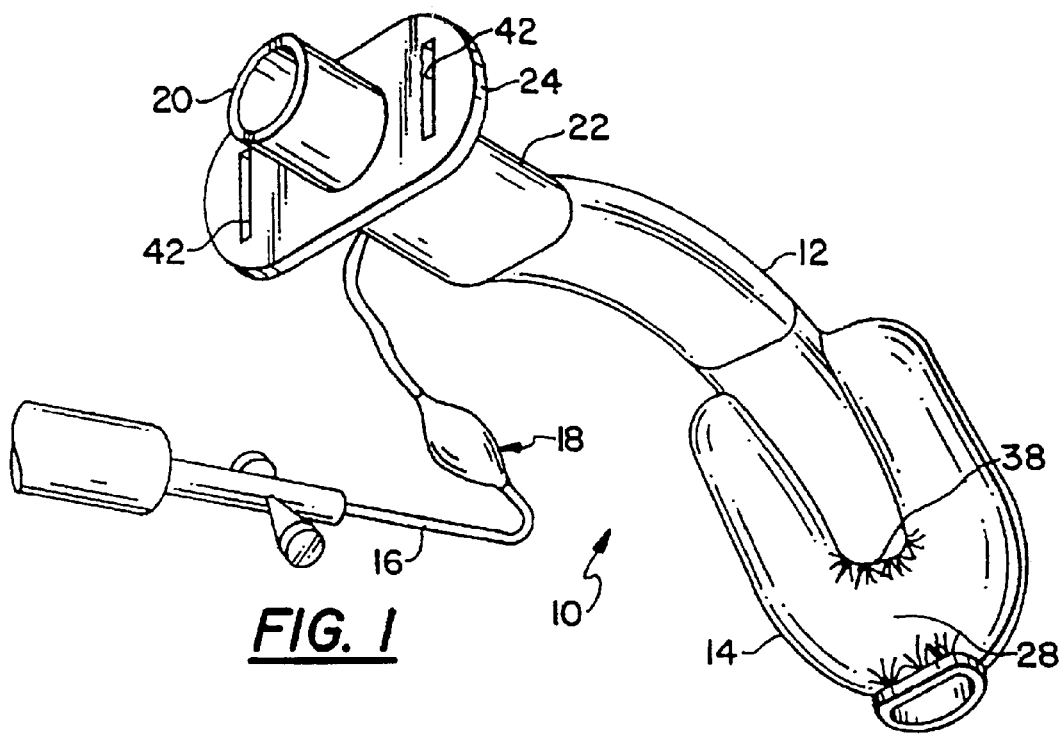
FIG. 1 is a perspective view of a cuffed oro-pharyngeal airway that may be used as an adjunct to fiberoptic endotracheal intubation in accordance with the present invention.
Figure 2:
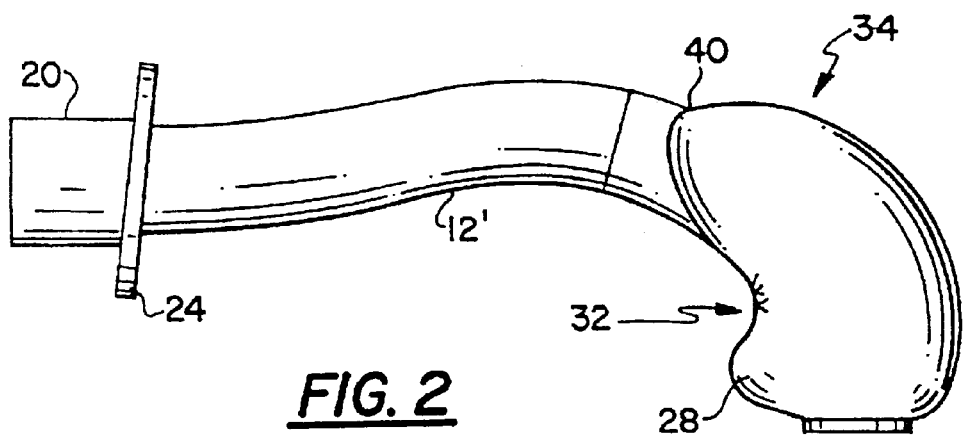
FIG. 2 is an elevational view of another airway configuration that may be used in accordance with the present invention.

In accordance with the invention, a Guedel-type oral airway or a similarly-configured cannula 12, 12' having an inflatable component 14 which is selectively inflated through tube 16 and check valve 18, is used to establish a supported airway during fiberoptic oral or nasal intubation. The illustrated structure is described in detail in U.S. Pat. Nos. 5,653,229 and 5,443,063.

At the proximal end of airway 12, 12', a connector 20 is provided to couple the airway to an anesthesia or other ventilation circuit. A bite block 22 and/or tooth/lip guard 24 are also preferably provided at the proximal end. The lip guard 24 may have ears with apertures 42 and/or hooks for strap attachment.

In the illustrated embodiment, on inflation, the inflatable component or cuff 14 defines a ventral/anterior projecting portion 28 which anteriorly displaces the base of the tongue 30 so that the tongue may rest against the seat 32 created by portion 28. The posterior side 34 of the device supports the device in the oral cavity and seals with the pharyngeal tissues to minimize leakage around the device. Attachment at 38 and 40 restricts movement of the cuff 14.

Fiberoptic endotracheal intubation in accordance with the invention may be performed through one of the nares as a nasal intubation or through the mouth for oral intubation. Both procedures are described in detail hereinbelow.

An exemplary intubation procedure in accordance with the invention is as follows:

Prepare the fiberoptic scope 50 by preloading an endotracheal tube (not shown). Specifically, the fiberoptic scope 50 is threaded through the endotracheal tube and the endotracheal tube is positioned high/proximal on the scope. This leaves the distal tip of the scope free for insertion into the patient and manipulation. Any size endotracheal tube which can be positioned on the fiberoptic scope can be used; the size of the COPA is irrelevant thereto. Moreover, the endotracheal tube may be either cuffed or uncuffed. If the tube is cuffed, the cuff should be deflated and smoothed back distally.

Position the patient supine with IV and monitors in place and preoxygenate and premedicate as deemed necessary or desirable. Then induce anesthesia using, for example, either an intravenous or inhalational anesthetic. Alternatively, regional airway blocks may be performed and the patient thus remains awake.

Insert the COPA 10 and inflate the cuff 14 according to the package directions. Secure the strap to hold the COPA in place. Attach the circuit and assist ventilate with oxygen as necessary.

It is possible to establish continuous positive airway pressure (CPAP), e.g. about 10–20 cm $H_2O$, by closing off the pop-off valve on the circuit. At this point, the patient is spontaneously breathing with the COPA supporting the airway.

Figure 3:
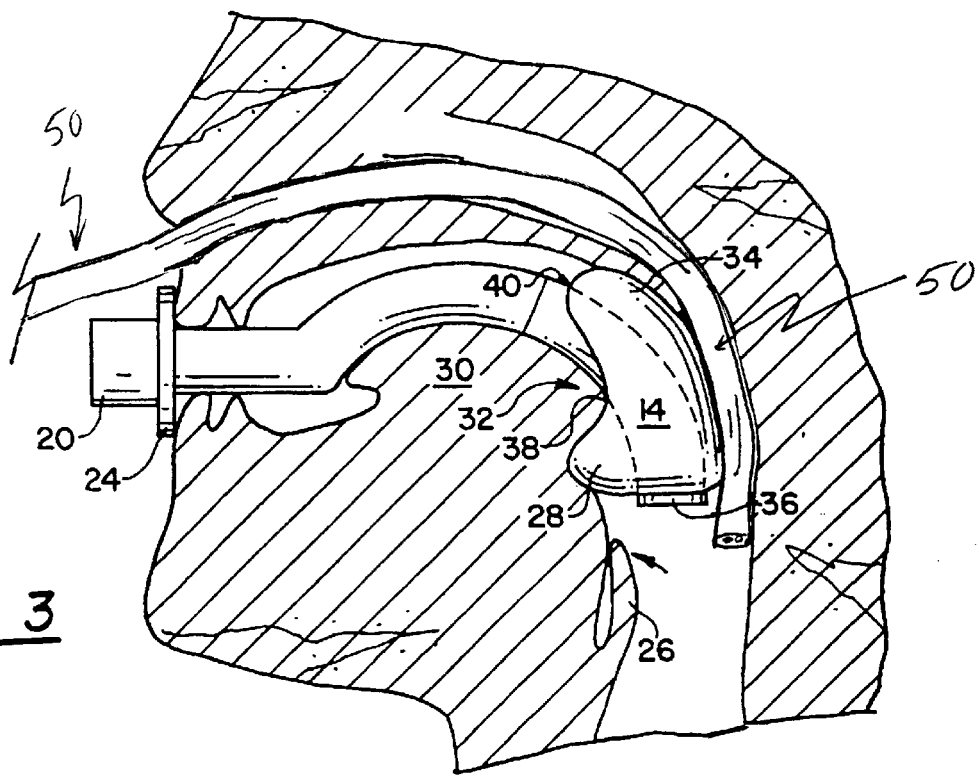
FIG. 3 is an elevational view showing a cuffed oro-pharyngeal airway (COPA) disposed within the patient's oral cavity and with the cuff inflated, and wherein a fiberoptic scope is fed through one of the nares and fed down behind the soft palate.
Figure 4:
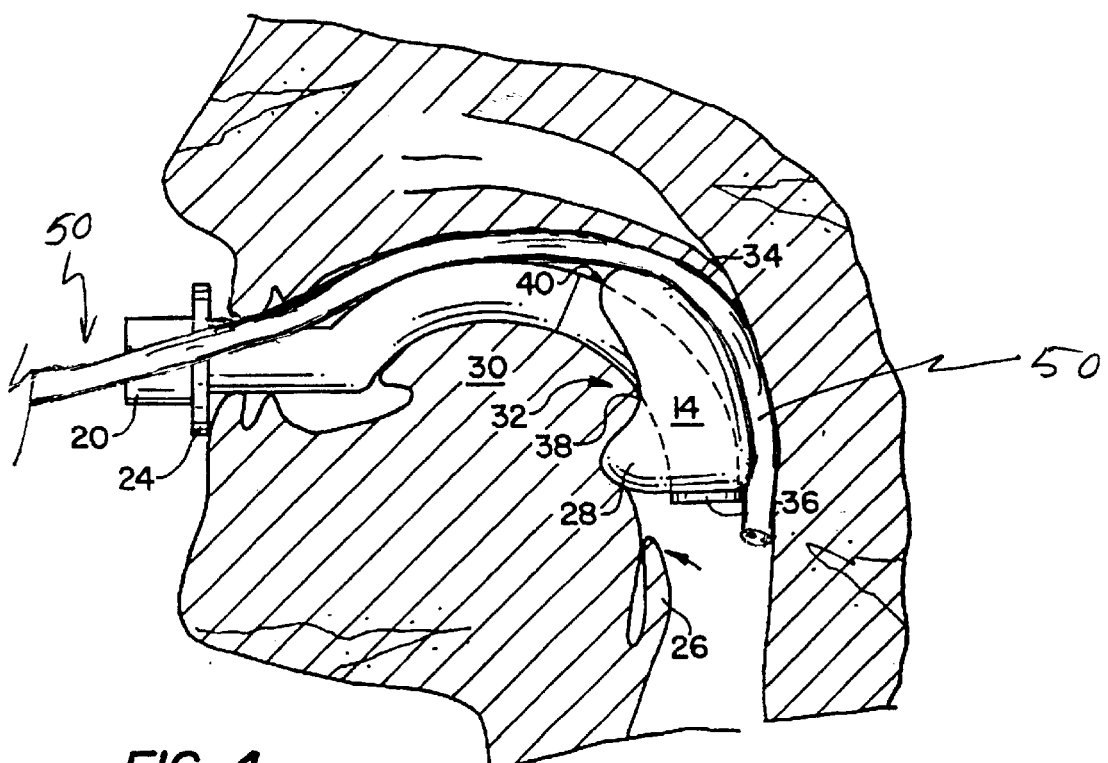
FIG. 4 is an elevational view showing cuffed oro-pharyngeal airway (COPA) disposed within the oral cavity and with the cuff inflated, and wherein a fiberoptic scope is disposed between the COPA cuff and the pharyngeal wall.

While the patient is breathing with the COPA in place, place the tip of the fiberoptic scope 50 through one of the nares (or through another orifice such as the orbit, sinus) for nasal intubation (FIG. 3) or between the COPA cuff and the pharyngeal wall for oral intubation (FIG. 4).

Advance the tip of the fiberoptic scope beyond the distal edge 36 of the COPA cuff to emerge in the hypopharynx at the level just above the epiglottis 26 and vocal cords. If the cords are not visible at this point:

1) make sure that the scope hasn't turned or twisted and that the scope is contacting a tonsil;
2) make sure that the scope has not been advanced too far so as to be at the gastroesophageal junction or passed into the esophagus;
3) tip up the scope to look slightly more ventrally (vallecula);
4) tip the scope down to look posterior to the epiglottis;
5) advance the scope (the scope may not have cleared the COPA cuff);
6) lift the epiglottis by performing a simple head tilt or chin lift.

At this point, ideally, the patient is spontaneously breathing with the COPA supporting the airway and the scope enveloped by the postero-lateral (oral) or posterior (nasal) aspect of the inflated cuff. The seal of inspired and expired gas is not generally affected by the presence of the scope. The COPA cuff is compliant enough to seal around the scope and the wall of the pharynx.

Upon visualizing the vocal cords, it is preferable to deepen the general anesthetic or anesthetize the vocal cords and trachea locally.

Once the patient is prepared for tracheal stimulation, the trachea may be penetrated with the fiberscope. Pass the fiberoptic scope deeply enough into the trachea so as to be sure that the tip will not become dislodged with patient movement or small scope manipulations.

Hold the fiberscope in place and deflate the COPA slightly and pull the COPA almost completely out. By leaving the tip of the COPA at the teeth, e.g., left premolars and molars, it functions as a protective bite block to reduce risk of damaging the fiberoptic scope. Pass the preloaded endotracheal tube into the trachea using the fiberoptic scope as a stylet or guide.

Should the beveled tip of the endotracheal tube become caught on the posterior arytenoids, it may be helpful to rotate the tube 180° around the axis of the scope to position the bevel into the airway and make passage into the trachea easier.

At this point it is prudent to re-visualize the carina and observe the endotracheal tube (ETT) as one removes the fiberoptic scope, noting the presence and position of the ETT in the trachea. This allows confirmation that the ETT is in midposition of the trachea and provides the immediate opportunity to re-intubate if the patient is inadvertently extubated while removing the scope.

Completely remove the scope, inflate the ETT cuff and attach the circuit to the ETT. A positive end-tidal $CO_2$ will confirm that the ETT is in the trachea.

The deflated COPA may be left in the mouth of the patient as a bite block to protect inadvertent biting of the ETT.

EXAMPLE

The effectiveness of the device as an adjunct to fiberoptic endotracheal intubation was evaluated.

METHOD

Thirty-eight (38) adult patients undergoing general anesthesia were studied. Patients 42±17 years old, 72±15 kg (mean±standard deviation) received various anesthetic techniques including midazolam, alfentanyl, propofol (bolus and/or infusion), isoflurane (as maintenance). After achieving an adequate depth of anesthesia, an appropriately sized COPA (9 cm, n=16; 10 cm, n=15; 11 cm, n=7) was placed, strap applied, cuff inflated, and the patient allowed to spontaneously ventilate (confirmed by filling of the anesthesia bag, $ETCO_2$, and oxygen saturation). Eight patients (21%) then received vercuronium and were hand ventilated via the COPA. Laryngoscopy was then accomplished by passing the fiberscope along the outside of the COPA, between the inflated cuff and right posterior-lateral wall of the pharynx. Vocal cords were identified and, after the fiberscope was passed to the carina, the COPA was removed and a preloaded 7.0 mm cuffed ETT was positioned and secured in the trachea.

RESULTS

For this study, median time from initial placement of the scope in the airway to attachment of the anesthesia circuit to the ETT was 138 secs for all intubations, and 98 secs for nasal intubation, and decreased with experience.

The procedure was aborted in one patient due to copious secretions. Another patient experienced transient hypoxemia (low $SaO_2$=64%) secondary to coughing on passing the cords, without sequelae. No other potentially serious complications were associated with the procedure.

CONCLUSIONS

The COPA may be a useful adjunct to fiberoptic endotracheal intubation, allowing control and support of the airway during the procedure, using various anesthetic techniques, in an acceptable amount of time. The ability to perform fiberoptic endotracheal intubation while effectively supporting the airway using the COPA may be advantageous in managing the difficulat airway or teaching fiberoptic technique.

While the oral intubation procedure has been described with reference to the currently preferred process of inflation of COPA cuff before the fiberoptic scope is advanced into the patient's oral cavity, in the alternative, before insertion of the COPA, the fiberoptic scope is appropriately lubricated using lidocaine jelly or surgilube, or the like and is gently laid in the throat of the patient so that the tip is just past the uvula. In that event the scope will be up against the upper teeth, perhaps up against the right biscupid/canine and coursing into the mouth along the hard palate just to the right of the midline with the tip ending up next to but perhaps a centimeter beyond (deeper in the throat) than the uvula. Then the deflated cuff can be placed in the mouth so that the scope will be between the COPA and the right upper oropharynx. The COPA cuff is then inflated assuring that the base of the tongue is high up in the cup of the cuff so that the bulk of the base of the tongue rests above (proximal to) the ventral (smaller) portion of the cuff. The cuff is then inflated enough to seal the airway as would normally be done. Then the strap is secured and the circuit attached for ventilation. Again, e.g., about a 10–20 cm H₂O CPAP is established. At this point the visualization of the cords and subsequent steps of the process described above are undertaken to complete the endotracheal intubation procedure.

As is apparent from the foregoing, ventilation of the patient can be maintained throughout the intubation procedure and intubation can be performed by one person even in the event the patient is under general anesthesia.

Performance of fiberoptic intubation in a child can be performed using the same or similar techniques as with the COPA in the adult. An alternative to having the fiberoptic scope pass through the ETT would be to observe the endotracheal tube passing alongside or into the trachea by positioning the fiberoptic scope either within the COPA or alongside it. A distinct advantage of fiberoptic intubation using the COPA over the laryngeal masked airway (LMA) is that one does not need to blindly place the LMA into an area that is presumably abnormal, thus decreasing the risk of causing trauma to fragile mucosa, the hypopharynx, and laryngeal structures. An additional advantage is that one is not limited to a smaller sized ETT. ETT size becomes an issue, and a potential problem, when it is to be passed through the lumen of another device.

While the invention has been described in connection with what is presently considered to be the most practical and preferred embodiment, it is to be understood that the invention is not limited to the disclosed embodiments, but, on the contrary, is intended to cover various modifications and equivalent arrangements and procedures included within the spirit and scope of the appended claims.

What is claimed is:

1. A method for fiberoptic endotracheal intubation comprising:
    providing a device comprising a cannula having a first, distal end for placement within the pharynx of a patient, a second, proximal end adapted to be disposed outside of the patient's oral cavity, and a flow passage therebetween, that cannula having a length such that when the distal end is placed within the pharynx, it terminates distally at a point near the patient's epiglottis; and an inflatable cuff structure for forming a seal between a wall of said cannula and a wall of the patient's pharynx, said cuff being disposed adjacent said distal end and defining, on inflation, a ventral/anterior portion and a posterior portion;
    inserting said device, with cuff deflated, into a patient's mouth so that said distal end of said device is disposed at a point near the patient's epiglottis thereby to establish an airway column down the core of the device;
    inflating said cuff structure whereby the patient's airway is supported and at least one of spontaneous breathing and controlled ventilation through the flow passage of the device can thereafter be provided;
    providing a fiberoptic scope;
    preloading an endotracheal tube on the fiberoptic scope so that the fiberoptic scope is threaded through the endotracheal tube with a distal tip of the scope projecting beyond the endotracheal tube for insertion into the patient;
    inserting said fiberoptic scope through the patient's oral cavity so that the tip is in the throat past the uvula, whereby after insertion of said device and inserting of said fiberoptic scope, said fiberoptic scope is disposed exteriorly of said device;
    advancing the tip of the fiberoptic scope so that the fiberoptic scope tip enters the trachea;
    advancing the endotracheal tube through the oral cavity and into the trachea using the fiberoptic scope as a guide; and
    removing the fiberoptic scope from the trachea.

2. The method of claim 1, wherein said step of inserting a fiberoptic scope precedes said step of inserting said device.

3. The method of claim 1, further comprising the step of at least partially deflating the cuff of the device and displacing the device proximally, before said step of advancing the endotracheal tube, and wherein said step of displacing said device proximally comprises pulling the device almost completely out of the oral cavity so that the distal tip of the device is adjacent the teeth whereby said device defines a bite block to protect said fiberoptic scope.

4. The method of claim 1, wherein said step of inflating said cuff structure comprises inflating said cuff structure to seal the oro-pharynx, distend the upper pharyngeal structures to open further the pharyngeal airway column, and wherein said ventral/anterior portion is disposed on said cannula so as to displace, on inflation, a base of the patient's tongue, thereby locking said cannula in place in the pharynx.

5. The method of claim 1, wherein said step of providing a device comprises providing a device including a tooth/lip guard having means for attaching a stabilizing strap thereto and further comprising attaching a strap to the tooth/lip guard.

6. The method of claim 1, wherein said step of providing comprises providing a device with an inflatable cuff having a ventral/anterior portion comprising a protuberance having a length less than a length of said posterior portion.

7. The method of claim 1, wherein said step of providing comprises providing a device preformed to define a generally straight proximal portion and an upwardly arched intermediate portion.

8. The method of claim 1, further comprising forming said device from a semi-rigid material that resists kinking.

9. A method for fiberoptic endotracheal intubation comprising:
    providing a device comprising a cannula having a first, distal end for placement within the pharynx of a patient, a second, proximal end adapted to be disposed outside of the patient's oral cavity, and a flow passage therebetween, that cannula having a length such that when the distal end is placed within the pharynx, it terminates distally at a point near the patient's epiglottis; and an inflatable cuff for forming a seal between a wall of said cannula and a wall of the patient's pharynx, said cuff being disposed adjacent said distal end and defining, on inflation, a ventral/anterior portion and a posterior portion;
    inserting said device, with cuff deflated, into a patient's mouth so that said distal end of said device is disposed at a point near the patient's epiglottis thereby to establish an airway column down the core of the device;
    inflating said cuff structure, whereby the patient's airway is supported and at least one of spontaneous breathing and controlled ventilation through the flow passage of the device can thereafter be provided;

providing a fiberoptic scope;

preloading an endotracheal tube on the fiberoptic scope so that the fiberoptic scope is threaded through the endotracheal tube with a distal tip of the scope projecting beyond the endotracheal tube for insertion into the patient;

inserting said fiberoptic scope through the nasal cavity so that the tip is in the throat past the uvula;

advancing the tip of the fiberoptic scope so that the fiberoptic scope tip enters the trachea;

advancing the endotracheal tube into the trachea using the fiberoptic scope as a guide; and removing the fiberoptic scope from the trachea.

10. The method of claim 9, wherein said step of inflating said cuff structure comprises inflating said cuff structure to seal the oro-pharynx, distend the upper pharyngeal structures to open further the pharyngeal airway column, and wherein said ventral/anterior portion is disposed on said cannula so as to displace, on inflation, a base of the patient's tongue, thereby locking said cannula in place in the pharynx.

11. The method of claim 9, wherein said step of providing a device comprises providing a device including a tooth/lip guard having means for attaching a stabilizing strap thereto and further comprising attaching a strap to the tooth/lip guard.

12. The method of claim 9, wherein said step of providing comprises providing a device with an inflatable cuff having a ventral/anterior portion comprising a protuberance having a length less than a length of said posterior portion.

13. The method of claim 9, wherein said step of providing comprises providing a device preformed to define a generally straight proximal portion and an upwardly arched intermediate portion.

14. The method of claim 9, further comprising forming said device from a semi-rigid material that resists kinking.

15. The method of claim 9, further comprising at least partially deflating the cuff of the device and displacing the device proximally, before said step of advancing the endotracheal tube.

16. The method of claim 9, wherein said step of inserting the fiberoptic scope comprises inserting the fiberoptic scope through one of the patient's nares and through the nasal cavity.

17. A method for fiberoptic endotracheal intubation comprising:

providing a device comprising a cannula having a first, distal end for placement within the pharynx of a patient, a second, proximal end adapted to be disposed outside of the patient's oral cavity, and a flow passage therebetween, that cannula having a length such that when the distal end is placed within the pharynx, it terminates distally at a point near the patient's epiglottis; and an inflatable cuff structure for forming a seal between a wall of said cannula and a wall of the patient's pharynx, said cuff being disposed adjacent said distal end and defining, on inflation, a ventral/anterior portion and a posterior portion;

inserting said device, with cuff deflated, into a patient's mouth so that said distal end of said device is disposed at a point near the patient's epiglottis thereby to establish an airway column down the core of the device;

inflating said cuff structure, whereby the patient's airway is supported and at least one of spontaneous breathing and controlled ventilation through the flow passage of the device can thereafter be provided;

providing a fiberoptic scope having a distal tip;

providing an endotracheal tube;

passing the endotracheal tube alongside the device and into the throat past the uvula;

positioning the fiberoptic scope one of within said flow passage and alongside said device;

passing the endotracheal tube into the trachea; and observing the endotracheal tube at least one of passing alongside said device and passing into the trachea.

18. The method of claim 17, wherein said step of inflating said cuff structure comprises inflating said cuff structure to seal the oro-pharynx, distend the upper pharyngeal structures to open further the pharyngeal airway column, and wherein said ventral/anterior portion is disposed on said cannula so as to displace, on inflation, a base of the patient's tongue, thereby locking said cannula in place in the pharynx.

19. The method of claim 17, wherein said step of providing a device comprises providing a device including a tooth/lip guard having means for attaching a stabilizing strap thereto and further comprising attaching a strap to the tooth/lip guard.

20. The method of claim 17, wherein said step of providing comprises providing a device with an inflatable cuff having a ventral/anterior portion comprising a protuberance having a length less than a length of said posterior portion.

* * * * *